United States Patent [19]

Linder

[11] 4,248,236

[45] Feb. 3, 1981

[54] PACKAGED MEDICAL APPLIANCE

[76] Inventor: Gerald S. Linder, 16693 Charmel La., Pacific Palisades, Calif. 90272

[21] Appl. No.: 973,145

[22] Filed: Dec. 26, 1978

[51] Int. Cl.$^3$ .............................................. A61M 25/00
[52] U.S. Cl. ............................ 128/349 B; 128/350 R; 128/341; 206/364
[58] Field of Search ............... 128/351, 350 R, 349 R, 128/348, 214.4, 125–127, 341; 206/364

[56] References Cited

U.S. PATENT DOCUMENTS

| | | | |
|---|---|---|---|
| 3,612,038 | 10/1971 | Halligan | 206/364 X |
| 3,750,875 | 8/1973 | Juster | 206/364 |
| 3,957,055 | 5/1976 | Linder et al. | 128/341 X |

Primary Examiner—Stephen C. Pellegrino
Attorney, Agent, or Firm—B. F. Spencer

[57] ABSTRACT

A sterilized medical appliance is disclosed, consisting of a preassembled catheter or endotracheal tube with connector, guide, stop, and handle, packaged within a sealed envelope and ready for immediate use in case of emergency. The assembled and packaged appliance is gas-sterilizable within the sealed envelope. The guide positioned within the endotracheal tube serves to provide structural support and protection for the endotracheal tube during handling and shipping. The endotracheal tube surrounding the guide serves to reduce the risk of penetration of the sealed envelope by the distal tip portion of the guide. The envelope is composed of a tough, flexible, transparent, plastic material to permit visual inspection and to enable the manual configuration of the endotracheal tube, with guide inserted, into a desired shape for intubation without danger of rupture of the envelope and without loss of sterility.

9 Claims, 2 Drawing Figures

PACKAGED MEDICAL APPLIANCE

BACKGROUND OF THE INVENTION

The present invention relates to packaged medical appliances, and, in particular, to medical appliances which may be manually configured into a desired shape while sealed within a sterile, flexible envelope, without rupture of the seal and without loss of sterility.

The conventional method catheter consists of a long, flexible tube of pliable material, such as rubber or other suitable polymer, having a smooth, rounded open distal end, and an open proximal end. The catheter is intubated into a body orifice of the patient for the purpose of withdrawing body fluids. To accommodate the needs of the patient, a wide variety of types, sizes, and lengths of catheters are available to the physician. Catheters usually are individually sterilized and are packaged within a sealed, supporting structure for providing protection during shipping and handling.

The endotracheal tube is a type of catheter used by the anesthesiologist for intubation into the trachea of the patient in preparation for anesthesia. Endotracheal tubes may be smooth and uncuffed, or they may be of the cuff type, and a large variety of types, sizes and lengths are available to accommodate the needs of patients. The accepted medical procedure has been to package each endotracheal tube within its own individual sterilized pouch or container.

Standard connectors are generally inserted into the open proximal end of endotracheal tubes for ease of coupling the endotracheal tube to the anesthesia equipment. Such a connector frequently is packaged along with its mating endotracheal tube. Connectors also vary widely in sizes and types, and are available separately in sterilized containers.

The selection by the physician of a suitable catheter or endotracheal tube will be dependent upon the nature of the operation to be performed, the age and physical size of the patient, and the portion of the body to be intubated. Having selected a suitable catheter or endotracheal tube, as the nature of the operation may require, the physician must decide whether some form of guide or holder would help in intubating the catheter or endotracheal tube. A number of guides or aids are available to the physician for providing stiffening, guidance or mechanical rigidity to the flexible catheter or endotracheal tube. Such guides or aids are available in a number of sizes and lengths and generally are individually packaged and sterilized in their own containers. One example of a guide provided with an adjustable stop and handle is disclosed in U.S. Pat. No. 3,957,055.

Where a guide with adjustable stop is to be used with the selected catheter, it is necessary for the physician to assemble the appliance in preparation for intubation. This assembly calls for the steps of breaking the seal of the container supporting the guide, withdrawing the sterilized guide, determining the depth of penetration of the guide into the catheter, adjusting the position of the stop upon the guide, locking the position of the stop upon the guide, breaking the seal of the pouch to the catheter, inserting the distal end of the guide into the hollow, flexible catheter, and withdrawing the assembled appliance from the pouch. A similar procedure is followed for endotracheal tubes, and each of the steps in the procedure must be carried out without compromising the sterility of the appliance.

While the above-described procedure allows the maximum degree of flexibility to the physician in selecting a catheter, endotracheal tube, connector and guide from among the various types, sizes and lengths, it is not without its problems and shortcomings. The procedure is tedious, time-consuming and costly. Not only is there a risk of loss of sterility in assembling the appliance, there also may be a serious loss of time in attempting to locate the needed elements in emergency situations where time is crucial. This is especially true in accident cases where the patient must be intubated promptly with the correct endotracheal tube in preparation for anesthesia. The present invention overcomes the above problems and provides substantial improvements in packaged medical appliances.

A principal object of the present invention is to provide an assembled medical appliance sealed within a sterile envelope and ready for immediate use.

Another important object is to provide an assembled catheter with guide and stop sealed within a sterilized, flexible envelope and which may be manually configured into a desired shape without rupture of the envelope and without loss of sterility.

Another object of the invention is to reduce the cost of medical appliances which must be discarded after a single use.

DESCRIPTION OF THE INVENTION

Figure 1:
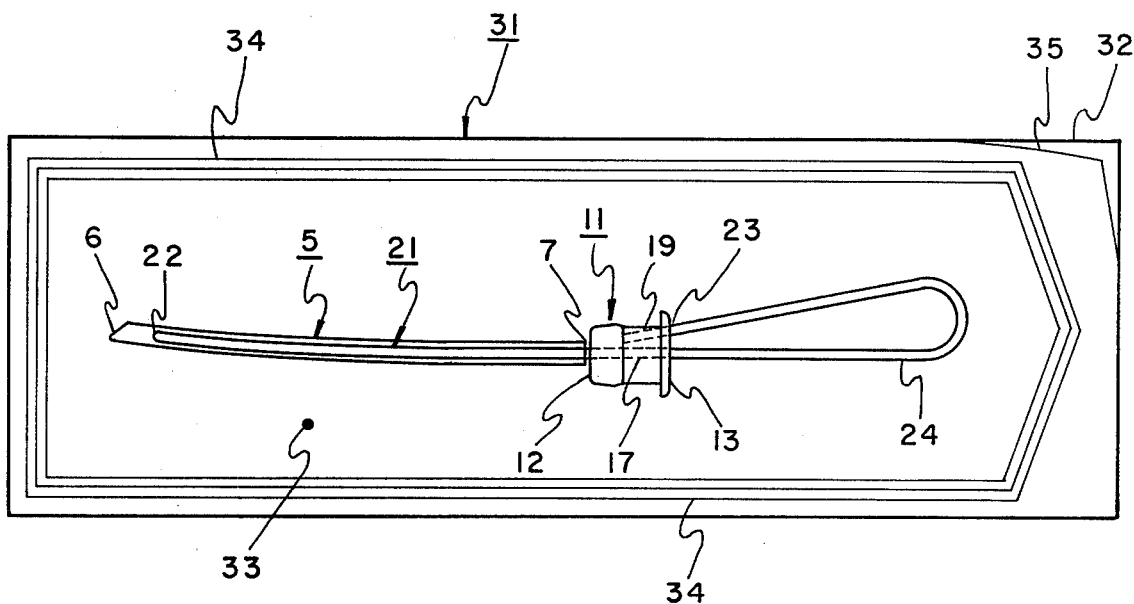
FIG. 1 illustrates an assembled medical appliance, consisting of a catheter with catheter guide, stop and handle, packaged in accordance with the preferred embodiment of the invention.

Referring to FIG. 1, a medical appliance is shown, consisting of a long, hollow, cylindrical catheter 5 of pliable material, having a rounded, open distal end 6 and a flat open proximal end 7. Catheter 5 may be formed from a transparent or semi-transparent tube of highly flexible plastic or polymer material. A cylindrical stop 11 of resilient material, having a first flat end surface 12 and a second flat end surface 13, is situated adjacent the proximal end of catheter 5, with flat end surface 12 abutting the proximal open end 7. A central bore 17 extends coaxially through stop 11 between end surfaces 12 and 13. A cylindrical hole 19 extends partially into stop 11 from end surface 13. Hole 19 is substantially parallel to and laterally offset from central bore 17.

A long, thin catheter guide 21, consisting of a polymer-coated wire of malleable material, having a smooth, rounded distal end 22 and a proximal end 23, extends through and is centrally supported by bore 17 of stop 11. The portion of the length of catheter guide 21 between stop 11 and distal end 22 is situated within hollow, flexible catheter 5. The depth of penetration of guide 21 within catheter 5 is predetermined by the adjustment of the position of stop 11 along the guide, such that distal end 22 remains within catheter 5 near its open distal end 6. Guide 21 is similar to the guide disclosed in U.S. Pat. No. 3,957,055.

The portion of the length of catheter guide 21 between stop 11 and proximal end 23 is formed into a smooth handle 24, with proximal end 23 being forceably inserted into the laterally-displaced cylindrical hole 19.

The insertion of proximal end 23 of guide 21 into hole 19 provides a secure anchor for the handle 24 while causing a clamping force to be applied by bore 17 of stop 11 upon the surface of guide 21, as taught and claimed in my co-pending U.S. Pat. application Ser. No. 890,401 filed Mar. 27, 1978 now U.S. Pat. No. 4,185,639.

Sterilization tests using the conventional ethylene oxide process of gas sterilization have established that the assembled appliance, including catheter 5 with open distal and proximal ends, inserted guide 21, and stop 11 with handle 24, can be successfully sterilized while sealed within a suitable gas-permeable envelope. The assembled appliance is placed in such an envelope 31, having a substantially rectangular backing or rear surface 32 and a transparent overlay or front surface 33. Rear surface 32 may be composed of tough, though flexible, plasticized paper material, and one suitable material is marketed under the trademark TYVEK by E. I. Dupont Company. The overlay, or front surface 33, may be formed from polyethylene or polyester film, and one suitable film is marketed under the trademark MYLAR.

After placement of the assembled appliance within envelope 31, the envelope is completely sealed by thermal bonding, indicated by lines 34. Three separate and independent bonded seals are indicated by the three parallel lines 34 to assure a strong seal. A portion of front surface 33, outside of the sealed area and adjacent one end of envelope 31, forms a flap 35. Flap 35 enables the front surface 33 to be peeled away, thereby rupturing the seals and providing easy access to the appliance.

Figure 2:
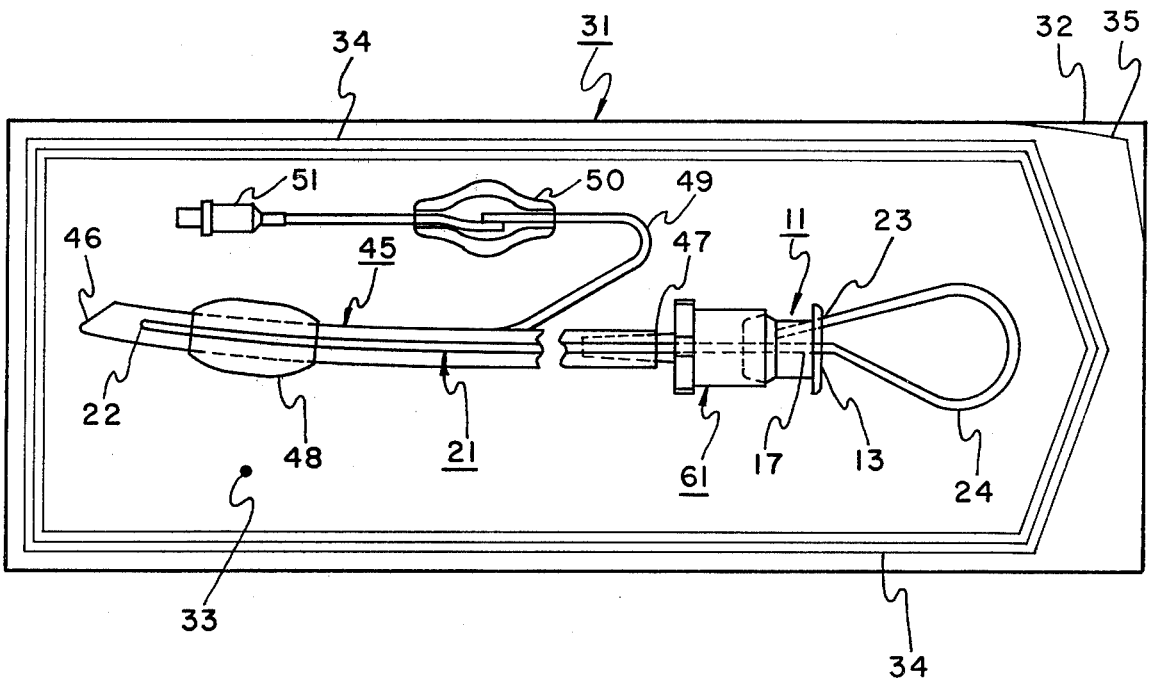
FIG. 2 illustrates an endotracheal tube with connector, guide, stop and handle preassembled and packaged within a flexible envelope and ready for immediate use in accordance with the invention.

The assembled catheter, guide, stop and handle of FIG. 1 is representative of a number of types of medical appliances which may be preassembled in preparation for intubation into patients. The anesthesiologist, for example, may employ an endotracheal tube with connector, guide, stop and handle for intubation into the trachea of the patient in preparation for anesthesia. FIG. 2 illustrates such an appliance assembled and packaged in accordance with the invention.

A conventional, flexible endotracheal tube 45 of the cuff type is provided with a rounded or beveled open distal end 46 and a flat open end 47. A thin cylindrical cuff 48 is affixed to the outer surface portion of tube 45 near its open distal end. While shown in its inflated condition for purposes of illustration, cuff 48 is deflated prior to packaging and shipment. The interior of cuff 48 is coupled to a small, flexible pilot tube 49, a portion of which is embedded within the wall of endotracheal tube 45. Pilot tube 49 extends from the wall portion of tube 45 through conventional pilot balloon 50 to an inflation valve connector 51.

A conventional, cylindrical connector 61 is shown, having a spout section inserted into the open proximal end 47 of endotracheal tube 45. The open end of connector 61 receives and supports stop 11. A long wire guide 21 of malleable material extends through and is supported by bore 17 of stop 11, in the same manner as described above in connection with FIG. 1. Stop 11 is positioned upon guide 21 such that distal end 22 is positioned within endotracheal tube 45 near its open distal end 46. The portion of guide 21, situated between outside surface 13 of stop 11 and the proximal end 23, is formed into a handle 24 in the same manner as described above in connection with FIG. 1.

The endotracheal tube 45 with connector 61, stop 11 and guide 21 is placed within a tough, flexible envelope 31, having a rear surface 32 and a front surface 33. The envelope 31 is sealed, as indicated by lines 34, and a flap 35 is provided in the same manner as described in connection with FIG. 1. The appliance may be sterilized after it is packaged and sealed by the conventional ethylene oxide process of gas sterilization or by any other acceptable radiation process.

The invention of FIGS. 1 and 2 achieves a number of worthwhile improvements in the art of medical appliances. Preassembly of the cooperating elements provides a sterilized appliance ready for immediate use. The invention not only conserves the physician's time, but it also is enormously beneficial to an injured patient in case of emergency. The cost of the preassembled and packaged appliance is substantially reduced by the elimination of duplicate packaging of the individual elements, such as catheter or endotracheal tube, connector, guide and stop. The necessity for individually sterilizing each of the separately packaged elements is also eliminated by the invention, wherein the entire assembly is sterilized together resulting in a further reduction in the cost of the appliance.

An additional reduction in cost is achieved by the preshaping of the proximal end of the guide into a handle and the presetting of the desired depth of penetration of the guide within the catheter or endotracheal tube. This results in a reduction in length of the overall package over that normally required to package and ship the guide in its straight, unshaped configuration.

Recognizing that the catheter or endotracheal tube guide, along with its stop, provides structural support and protection for the catheter or endotracheal tube, the need for stronger or stiffer packaging normally required to provide protection during shipment is eliminated. Thus, envelope 31 may be formed of relatively tough and lightweight material.

The risk of penetration of the seals of the envelope 31 by the distal and proximal tips or end of the catheter or endotracheal tube guide is eliminated by the present invention. This feature results from the preforming of the smooth rounded handle 24 and the placement of the guide with stop within the catheter or endotracheal tube such that the distal end 22 of the guide cannot extend beyond the open distal end of the catheter or endotracheal tube. Thus, the elements of the combination cooperate to provide an improved packaged appliance, with the guide providing support and protection for the catheter or endotracheal tube, and with the distal tip of the catheter or endotracheal tube providing protection against the risk of penetration of the envelope by the distal tip of the guide.

An improvement of considerable importance to the physician is achieved by the invention in the use of flexible material for forming envelope 31 and by employing a transparent front surface 33. This enables the physician not only to inspect the assembled appliance before deciding upon its suitability for the operation, but also to manually configure the sterilized catheter with its inserted guide, while within the sealed envelope, into a desired shape for intubation. The manual configuration of the catheter and guide by the physician is achieved without risk of rupture of the seals or the envelope and without loss of sterility of the appliance. After being shaped for intubation, the assembled appliance remains sealed within its sterilized package available for immediate use.

Since many changes can be made in the above-described apparatus and many different embodiments of this invention could be made without departing from the scope thereof, it is intended that all matter contained in the above description or shown in the accompamying drawings shall be interpreted as illustrative and not in a limiting sense.

What is claimed is:

1. A packaged medical appliance comprising in combination:
    (a) an elongated, cylindrical catheter consisting of a flexible hollow tube having open distal and proximal ends;
    (b) a hollow connector having a cylindrical spout section of small diameter at one end and a cyindrical open end section of larger diameter at the other end, the cylindrical spout section being inserted into the open proximal end of said catheter;
    (c) a long catheter guide consisting of a wire of malleable material having rounded distal and proximal ends, a portion of the length of said catheter guide being situated within said hollow, cylindrical catheter, with the distal end of said catheter guide being positioned near the open distal end of said catheter;
    (d) a stop means affixed to said catheter guide, said stop means being supported by the cylindrical open end section of said hollow connector, said stop means being positioned along said guide to predetermine the length of the portion of said guide situated within said catheter at less than the length of said catheter and inserted connector to prevent the distal end of said guide from extending beyond the open distal end of said catheter, the portion of the length of said catheter guide situated outside said hollow cylindrical catheter and said hollow connector being formed into a shape for use as a handle, said handle having a smooth, rounded end; and
    (e) a flexible envelope of tough gas-permeable material completely enclosing and sealing said catheter, connector, guide and stop means; said catheter with connector, guide and stop means being gas-sterilizable within said gas-permeable envelope, the flexible distal end of said hollow catheter providing protection against rupture of said flexible envelope by the distal end of said catheter guide, said catheter guide providing structural support and protection for said hollow, flexible catheter during shipment, and said catheter and the portion of the length of said guide situated within said catheter being manually configurable into a desired shape for intubation while enclosed within said flexible envelope, the configuration being achieved without rupture of said envelope and without loss of sterility of said catheter, connector, guide and stop means, said flexible envelope having a peelable flap portion located at one end thereof adjacent the smooth, rounded end of said handle, the smooth, rounded end of said handle minimizing the risk of rupture of said flexible envelope during handling and shipment, said catheter with inserted connector, guide and stop means being ready for immediate use upon removal from said envelope by peeling away said flap thereby rupturing the seal.

2. The packaged medical appliance as defined by claim 1 wherein said elongated, cylindrical catheter is an endotracheal tube.

3. The packaged medical appliance as defined by claim 2 wherein said endotracheal tube is an inflatable cuff type.

4. The packaged medical appliance as defined by claim 1 wherein said long catheter guide consists of a polymer-coated wire of malleable material.

5. The packaged medical appliance as defined by claim 1 wherein said stop means affixed to said catheter guide is a cylindrical section of resilient material, and wherein a portion of the cylindrical section is inserted into the cylindrical open end section of said hollow connector for forming a mating fit.

6. The packaged medical appliance as defined by claim 1 wherein the proximal end of said catheter guide situated outside said hollow cylindrical catheter and said hollow connector is secured to said stop means.

7. The packaged medical appliance as defined by claim 1 wherein said flexible envelope is composed of a transparent, plastic material.

8. A packaged medical appliance comprising in combination:
    (a) an elongated cylindrical catheter consisting of a flexible hollow tube having open distal and proximal ends, said cylindrical catheter including a hollow connector means attached to the open proximal end of said catheter;
    (b) a long catheter guide consisting of a wire of malleable material having distal and proximal ends, a portion of the length of said catheter guide being situated within said cylindrical catheter with the distal end of said guide being positiond near the open distal end of said catheter;
    (c) a stop means affixed to said catheter guide, said stop means being supported by said connector means, said stop means being positioned along said guide to predetermine the length of the portion of said guide situated within said catheter at less than the length of said catheter with attached connector means to prevent the distal end of said guide from extending beyond the open distal end of said catheter, the portion of the length of said catheter guide situated outside said hollow cylindrical catheter being formed into a handle, said handle having a smooth, rounded end; and
    (d) a flexible envelope of tough gas-permeable material completely enclosing and sealing said catheter, guide, and stop means; said catheter with attached connected means, guide, and stop means being gas-sterilizible within said sealed, gas-permeable envelope; the flexible distal end of said hollow catheter providing protection against rupture of said flexible envelope by the distal end of said catheter guide, said catheter guide providing structural support and protection for said hollow, flexible catheter during shipment, and said catheter with inserted guide being manually configurable while enclosed and sealed within said flexible envelope for shaping without rupture of said envelope and without loss of sterility of said catheter with attached connector means, guide and stop means, said flexible envelope having a peelable flap portion located at one end thereof adjacent the smooth, rounded end of said handle, the smooth, rounded end of said handle minimizing the risk of rupture of said flexible envelope during handling and shipment, said catheter with attached connector means with inserted guide and stop means being ready for immediate use upon removal from said envelope by peeling away said flap thereby rupturing the seal.

9. The packaged medical appliance as defined by claim 8 wherein said elongated cylindrical catheter is an endotracheal tube having open distal and proximal ends.

* * * * *